United States Patent [19]

Clark, III

[11] Patent Number: 4,959,148
[45] Date of Patent: Sep. 25, 1990

[54] METHOD AND APPARATUS FOR SPECIFIC AFFINITY ENHANCED TRANSPORT BIOREACTOR

[76] Inventor: William T. Clark, III, No. 13, Park La., Folsom, La. 70437

[21] Appl. No.: 299,446

[22] Filed: Jan. 23, 1989

[51] Int. Cl.$^5$ ............................................. B01D 15/08
[52] U.S. Cl. .................................... 210/635; 210/645; 210/656; 210/688; 210/198.2; 210/507.1; 210/506; 210/912; 525/329.7; 435/182; 435/288; 422/131; 422/239
[58] Field of Search ............... 210/635, 645, 656, 688, 210/198.2, 502.1, 506, 912; 525/54.1, 329.7; 435/182, 288; 422/129, 131, 239

[56] References Cited

U.S. PATENT DOCUMENTS

| | | | |
|---|---|---|---|
| 3,859,169 | 1/1975 | O'Driscoll et al. | 425/182 |
| 4,048,064 | 9/1977 | Clark, III | 210/638 |
| 4,452,892 | 6/1984 | Rosevear | 435/182 |
| 4,452,918 | 6/1984 | Uchida et al. | 210/656 |
| 4,634,672 | 1/1987 | Baumgarten et al. | 435/182 |
| 4,855,353 | 8/1989 | Kurami et al. | 525/54.1 |

OTHER PUBLICATIONS

Albert, Adrien, *Selective Toxicity*, Methven & Co., 1968, pp. 320–321.
Peppas, Nikolaos A. (Ed.), *Hydrogels in Medicine and Pharmacy*, vol. 1, CRC Press, 1986, pp. 102–103.
Andrade, Joseph D., (Ed.), *Hydrogels for Medical and Related Applications*, American Chemical Soc., 1976, p. 25.
Chibata, Ichiro (Ed.), *Immobilized Enzymes*, Halsted Press, 1978, pp. 68–70.

*Primary Examiner*—W. Gary Jones
*Attorney, Agent, or Firm*—Berman, Aisenberg & Platt

[57] ABSTRACT

A method and apparatus for removing and/or modifying specific target substances in the blood is disclosed. The invention includes a column or chamber in which selected bioreactant molecules are suitably retained for reaction within a porous hydrogel polymer matrix by reversibly quenching the reactant propensity with a displaceable surrogate and polymerizing an insoluble cross-linked hydrogel in such manner that the hydrogel polymer replicates the shape of the bioreactant molecule. This replicated phantom shape in the polymer then exhibits profound dispersion-force affinity for the bioreactant. The invention provides for retention of a wide variety of therapeutic reactants and reaction products while confining the reaction within the column.

67 Claims, 1 Drawing Sheet

METHOD AND APPARATUS FOR SPECIFIC AFFINITY ENHANCED TRANSPORT BIOREACTOR

BACKGROUND AND SUMMARY OF THE INVENTION

Biocompatible hemoperfusion, the technique of passing blood through an extracorporeal adsorbent column for the purpose of removing diverse waste metabolites and other toxic substances has become a widely used, safe, life-saving extracorporeal blood detoxification treatment of choice. However, as the biochemistry of major organ failure has become better understood, and as the toxic sequellae (and enormous therapeutic potential) of ever-more-complex chemotherapies have been revealed, the need to selectively and efficiently remove and/or modify specific target substances in the blood has become acute.

While the need for such an enhanced fixed-bed bioreactor has become apparent, the means of providing such a device have remained elusive until the present invention. Indeed, a bioreactor suitable for hemoperfusion presents formidable requirements.

The device must provide exquisite biocompatibility (sterility, antithrombogenicity, etc.) while quickly, efficaciously, and safely removing and/or modifying the target substance and/or reaction product.

Previous attempts to design a suitable blood-perfuseable target bioreactor have been unsuccessful essentially because of two major failings: (1) the devices were insufficiently biocompatible (even when such matters as thromboresistance and damage to formed blood elements were considered at all), and (2) the reactants either did not work or dangerous reactants or reaction products were not contained within the device.

Such previous attempts generally envision a scheme wherein blood is pumped through a fixed polymer bed loaded with the bioreactant. Unfortunately, in practice, this approach has not worked, either because when the reactant is immobilized the polymer prevents reaction of the immobilized bioreactant, or because the polymer is inappropriately porous ("leaky"), and the reactant and/or reaction product leaches out, dangerously releasing hazardous substances into the general circulation. Were these difficulties and others to be overcome, a valuable new extracorporeal therapy could be realized.

Accordingly, it is a primary object of this invention to provide a means of retaining a wide variety of therapeutic reactants and reaction products within a fixed biocompatible hemoperfusion columnar bed while confining full, efficacious, and safe reaction within the column for the purpose of curing disease and sustaining life. It is a further object of this invention to selectively sequester with enhanced efficiency certain target toxic substances and reaction products. It is a still further object of this invention to provide a bioreactor which can be easily and safely sterilized and manufactured.

These and other objects and benefits of the invention will be more fully understood as the invention is set forth and when distinguished from prior art.

Hemoperfusion became a widely-used, life-saving procedure when it was shown in U.S. Pat. No. 4,048,064 to Clark, which patent is incorporated herein by reference, that heparin could be entrapped in a hydrogel, thereby rendering antithrombogenicity and other desirable biocompatible characteristics. Entrapment is a suitable technique for heparin, because heparin activity does not depend upon chemical reaction. This entrapment technique is unsuitable for bioreactants, however, because activity will be impeded in proportion to the extent that the reactant is retained by this entrapment technique which relies on a polymer barrier that has pores smaller than the bioreactant. On the other hand, if a conventional hydrogel is made more porous in order to increase activity, then the bioreactant will escape. It is therefore necessary to provide a means of producing an extremely porous hydrogel which exhibits a powerful avidity for the bioreactant.

In this way, large organic molecules can freely perfuse the gel in order to react with the bioreactant retained by the gel which would be impossible with a prior art gel which simply entraps on the basis of size, because large molecules cannot pass the pore-size "barrier."

The principle of operation of the invention is not complex:

Selected bioreactant molecules are suitably retained for reaction within a porous hydrogel polymer matrix by reversibly quenching the reactant propensity with a displaceable surrogate and polymerizing an insoluble cross-linked hydrogel in such manner that the hydrogel polymer replicates the shape of the bioreactant molecule. This replicated phantom shape in the polymer then exhibits profound dispersion-force affinity for the bioreactant.

The quenching surrogate latentiates the reactive propensity of the bioreactant. The bioreactant is "quenched," because reaction with the monomer is prevented by the "surrogate" which alters the relative solvations of the solution components. Reaction thus prevented, it turns out that the polymer forms around the bioreactant with sufficient intimacy to replicate its shape, but without chemically attaching to it or embedding it (which would render it useless).

The bioreactant is thereby rendered accessible with full activity, unencumbered by steric hindrance from polymer embedment or undesirable reaction with functional groups. If desired, the bioreactant or biomolecule may even be extracted, the gel of phantoms then becoming a specific adsorbent for the biomolecule of interest. The enhanced affinity gel may also be used in combination with or coated over conventional solid adsorbents and substrates, such as activated carbon or reticulated foam.

Regardless of the application, of course, the gel must replicate the shape of the bioreactant and thus retain it while remaining porous. Porosity of the hydrogel is determined by the amount of water or other polymer nonsolvent present as the gel network is formed. If the water content is too high, the resulting gel will have poor mechanical properties or will not form at all; conversely, if the water content is too low, the gel will be insufficiently porous. The best replicating gels for biological use generally contain between 20% and 80% by weight of water. For most such gels, approximately 50% to 60% water is preferred. Such a gel will readily permit passage of proteins and high organic toxins. Replication occurs as the polymer retracts while polymer cross-links develop and at least part of the non-solvent is expelled. Cross-linking by chain transfer is preferable in order to maintain intimacy with the bioreactant thus assuring replication. Exogenous cross linking, with a copolymer for example, should be kept below 5% and preferably in the range of 1% to 3%.

DESCRIPTION OF THE PREFERRED EMBODIMENTS

Figure 1:
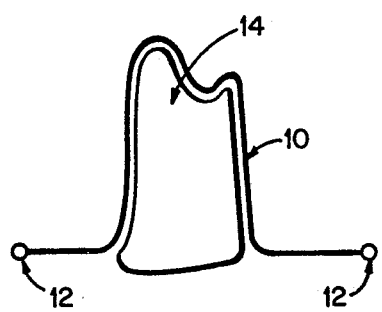
FIG. 1 is a simplified schematic illustration of the invention.

Reference is made to the greatly simplified schematic illustration of FIG. 1 where a single polymer chain 10 is shown between cross-links 12. The retracted polymer chain has encountered the bioreactant 14 thus replicating its shape.

Bioreactants suitable for use with this invention include any biomolecule capable of effecting the desired reaction and distinguishable by shape (a common distinguishing characteristic of organic biomolecules) with "shape" meaning field morphology giving rise to distinctive topography. Indeed, life itself may be said to exist because such shape specificity is essential for directing biochemical organic synthesis. Suitable bioreactants include, for example, chelating and complexing agents, lake formers, inclusion compounds, antigens, antibodies, mucopolysaccharides, antibiotics and enzymes.

Hydrogel polymers suitable for use with this invention may be any of a wide variety characterized by inertness in the biological environment and whose porosity, hydraulic permeability, and other diffusion characteristics can be predictably adjusted to allow fluid blood access to the bioreactant. Suitable hydrogels include, for example, the poly(alkyl)methacrylates, polyacrylamides, their homologues and derivatives.

The quenching surrogate is selected according to its ability to quench or prevent reaction of the bioreactant with the hydrogel during polymerization and according to its ability to affect solvation. The quenching surrogate is further characterized by its ability to be displaced or extracted from the bioreactant solution after polymerization is completed in order to allow the target reaction. The quenching surrogate, of course, should be biologically harmless when displaced. Suitable quenching surrogates may include such substances as, for example, ions or pseudo-functional moieties displaceable in solution, synthetic plasma extenders or substitutes such as polyvinylpyrollidone, and partitioning agents such as cyclodextrins.

For most bioreactants and quenching surrogates, an approximate ratio of 1:1 is preferred, although the exact ratio may vary widely for different substances. In any event, the concentration of an electrolytic quenching surrogate should ordinarily not constitute more than 5% of the water content of the monomer-water mix or the phases will tend to separate at between 5% and 10% concentration. On the other hand, as the concentration of quenching surrogate approaches 0.2% or less, polymerization will not occur or the bioreactant will be rendered inactive for the target reaction. It is desirable that the concentration of the quenching surrogate be osmotically normal (physiological).

The following preferred examples will further illustrate the principles and practical application of the invention.

EXAMPLE 1

Deferoxamine mesylate is a chelating agent bioreactant long used for the therapeutic life-saving reduction of toxic levels of iron and aluminum from the human body. However, the drug is unstable in solution, difficult to sterilize, and it can cause many harmful side-effects, especially dangerous to an already compromised patient. It is therefore extremely desirable to avoid introducing the drug systemically. Instead, the present invention makes it possible to retain this bioreactant in an extracorporeal column through which blood can be perfused, and the harmful life-threatening iron and aluminum can be removed from the blood without danger to the patient.

Deferoxamine mesylate is also a powerful inhibitor of polymerization and can easily enter into side reactions. It must therefore be quenched with a displaceable surrogate.

The following ingredients are dissolved in an inert vessel:

| | | |
|---|---|---|
| Bioreactant | Deferoxamine Mesylate | 250 mg. |
| Quenching Surrogate | 0.9% Sodium Chloride | 25 ml. |
| Initiators | 6% Ammonium Persulfate | 0.75 ml. |
| | 12% Sodium Metabisulfite | 0.75 ml. |
| Anticoagulant | Sodium Heparin 10,000 u/ml | 1 ml. |
| Monomer | 2-Hydroxyethyl Methacrylate | 22.5 ml. |

The solution can be briefly heated in order to hasten polymerization (approximately 70° C. for 1 minute) until polymerization begins. Heat is withdrawn and polymerization allowed to continue at room temperature. The expelled water is drawn off and the gel can be removed from the vessel. The gel will be in the form of a casting reflecting the shape of the vessel in which it was cast. The gel is placed into a blood-perfusable column. The assembled column is steam-sterilized. After cooling and washing it with heparinized normal saline, the column is ready for use.

Of course, the amount of bioreactant and quenching surrogate may be varied widely according to the dose required. The amount shown here has been found suitable for most applications.

Figure 2:
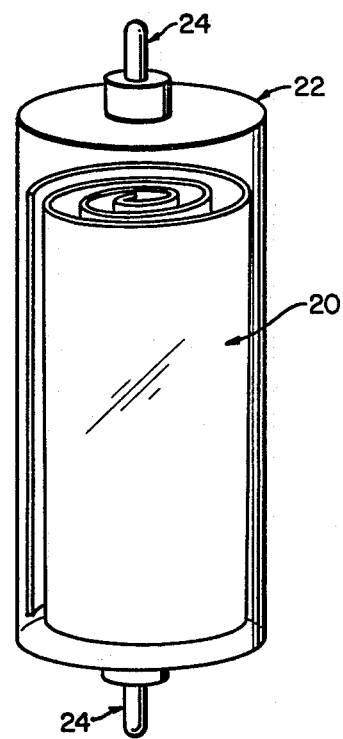
FIGS. 2-4 are illustrations of different embodiments of the invention.
Figure 3:
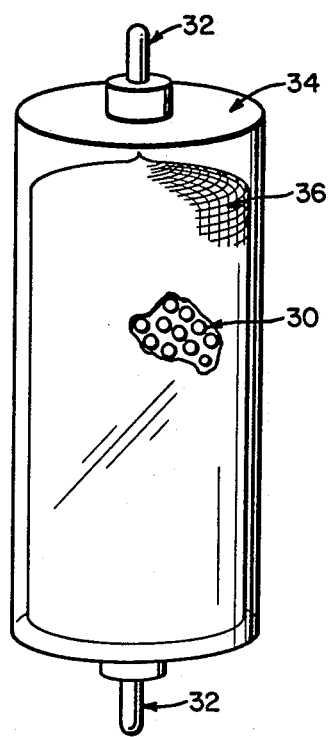

In this example, the cast gel is placed into the extracorporeal column always with the foremost consideration that the flowing blood should have easy access to the gel. For example, as in FIG. 2 a flat sheet of the gel may be wound into a spiral scroll 20 and loaded into a suitable hemoperfusion chamber 22, outfitted with blood line connectors 24 which allow blood to pass through the column. Still another method is shown in FIG. 3 where the gel has been cast or otherwise formed into small pellets 30. In order to prevent escape of very small gel pellets 30 past the blood line connectors 32, it is necessary to provide means to confine the pellets 30 within the hemoperfusion chamber 34, such as an elastic mesh sack 36 with mesh-size interstices smaller than the pellets 30.

EXAMPLE 2

Hydrogels made according to the principles of this invention have vastly improved mechanical properties exhibiting, for example, several hundred percent greater elastic elongation before fracture. This is due to the "kink" introduced into the polymer chains by the shape replication. Such improved properties enable the use of hydrogels in novel applications not heretofore possible with conventional hydrogels, such as in the form of elastic foams or sponges.

While this hydrogel can be foamed by such conventional methods as catalyst systems or bubbled inert gases under pressure, such methods may easily interfere with the replication process by evolving great heat or untoward chemistry. A preferred method is to sorb the monomer-bioreactant solution onto an elastic reticulated foam substrate.

In this example, reticulated regenerated cellulose foamed to a density of 1 gram per cubic inch is used.

Four cubic inches (in any desired shape or configuration) of such a foam is immersed in the formulation of Example 1. The wet foam is then transferred to an oven and cured at 150° F. until polymerization is complete (about an hour). The hydrogel-coated foam is then ready for use after removal of the expelled water (the foam will be moist), sterilization, and perfusion with saline. Alternatively, the foam may be left in the oven until completely dry (which is preferred if the foam is to be stored for a long period and not used immediately).

Figure 4:
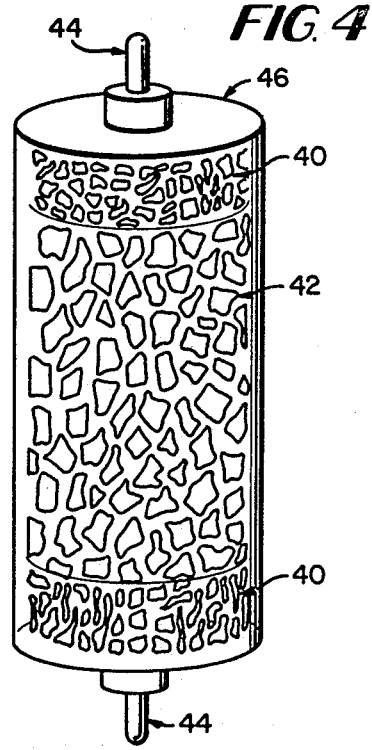

Such a foam can be used in a column alone, or it may be used as shown in FIG. 4 where the gel-coated foam 40 is in series with another granular adsorbent 42 such as activated carbon, thereby providing a mixed-bed of adsorbent techniques. When the elastic hydrogel-foam 40 is hydrated it will expand, fortuitously compressing the adsorbent granules 42, containing and immobilizing them, thus preventing their escape past the blood line connectors 44 into the general circulation while also preventing the generation of fines.

Yet another advantage of the expansible hydrogel-foam is its ability to conform to and fill any remaining available space in the column 46 without introducing deleterious pressure drop while greatly reducing the extracorporeal blood volume and simultaneously preventing any possibility of thrombus formation.

A still more important advantage of the hydrogel-foam, however, is that the column may be loaded with a series of such foams, each containing a different bioreactant. In this way a series of discrete biochemical operations can be conducted in a particular order as the blood passes through the column, thereby closely simulating the function of a vital organ. In addition, of course, bioreactants which would otherwise be incompatible in the same solution can be safely incorporated into the same column by the use of such discrete foams.

EXAMPLE 3

It is very frequently desirable to combine the bioreactant gel with a broad-spectrum solid adsorbent in order that toxic substances, including waste metabolites or reaction products not sequestered by the bioreactant, may be removed at the same time. The solid adsorbent substrate material could be any of various conventional adsorbents such as activated carbon, alumina and the like. This is a common necessity where severely ill patients have multiple organ failure and other diverse abnormalities. In this application, the superior porosity and transport characteristics of the bioreactant gel are distinctly important, because the toxic substance may well be attached to a very large carrier, such as a protein, which could not penetrate ordinary small-pore hydrogels.

In order to assure that the bioreactant remains active, it must not be permitted to penetrate the recesses of the adsorbent prior to the target reactive event. Indeed, the bioreactant used in this example, deferoxamine mesylate, becomes completely inactivated when adsorbed, losing entirely its ability to chelate metals. In order to prevent premature adsorption of the bioreactant, it is therefore necessary to introduce a competitively adsorbed solvent into the monomer-bioreactant mixture along with the other ingredients. The competitively adsorbed solvent keeps the bioreactant and other ingredients of the monomer solution out of the small-pore inner reaches of the adsorbent during polymerization which proceeds normally on the large-pore surface areas of the adsorbent. After polymerization and replication is complete, thereby retaining the bioreactant, the competitively adsorbed solvent is removed, then permitting adsorption of the molecules of interest. An excellent solvent for this purpose is ethyl alcohol, though other solvents or solvent combinations such as acetone can be used.

To the ingredients of the formulation of Example 1 add:

Competitively adsorbed solvent—Ethyl alcohol—200 ml (this amount may vary widely according to the fluid retention of the particular activated carbon).

Dip into this solution 240 grams granular activated carbon (12×40 mesh) until the evolution of heat ceases.

The wet granules are spread out on a tray and placed in a vacuum oven at approximately 150° to 200° F. for approximately 90 minutes.

When cooled, these granules are then placed in a fixed bed extracorporeal column and steam sterilized. After washing with a perfusate of heparinized normal saline, the granules are ready for blood perfusion.

Of course, ethyl alcohol is not compatible with all bioreactants, and in that event another competively adsorbed solvent may be used instead, or the competitively adsorbed solvent may be applied to the activated carbon prior to the application of the other ingredients.

EXAMPLE 4

In this example, the deferoxamine mesylate is removed from the hydrogel of any of the other examples by immersing the hydrogel into a solvent capable of extracting deferoxamine mesylate. Such a solvent is, for example, ethyl alcohol irradiated with ultrasound sufficient to cause cavitation. An indicator (such as ferric chloride) may be used in the solvent to indicate by color change when the removal has reached a practical end point. The gel should then be rinsed and dried. After washing and sterilization as in the other examples, the gel of phantoms is ready for use to remove any target molecule which will fit the shape, including systemically administered deferoxamine mesylate.

While the foregoing examples demonstrate the principles of the invention with a metal chelating agent, those skilled in the art will quickly recognize that such coordination compounds mimic the mode of action of an enormous range of therapeutic biologicals, such as antibiotics and anti-neoplastic agents. Prior to this invention, such bioreactants have been impossible to efficaciously retain. Chelating agents, for example, have long been known not to function at all if conventionally attached or if proximal to a bulk substrate, because they are unable to coordinate. This invention makes such retention possible, and the examples above must be seen as illustrative, not limiting.

Indeed, heparin, another biomolecule, is shown here retained by the examples of this invention, even though it has been shown to be retained by prior art methods as well. This new method for retention of the biomolecule offers the previously unavailable and very great advantage of heparin retention in combination with vastly improved transport, because transport through the gel is no longer limited by constraints of small pore size.

Because the gel has replicated the shape of the bioreactant, the hydrogel when permeated by biological fluids will have the unusual property of selective retention of the bioreactant while remaining porous. Uniquely, the porosity will be greater than the size of the bioreactant which it retains.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A bioreactor capable of retaining therapeutic reactants and reaction products while confining reaction within the bioreactor comprising:
   a chamber; a hydrogel polymer within said chamber; and a bioreactant within said chamber, said bioreactant having been quenched by a displaceable surrogate material so that said hydrogel polymer forms around the bioreactant with sufficient intimacy to replicate its shape but without chemically attaching to or embedding said bioreactant.

2. The bioreactor of claim 1 wherein said hydrogel polymer contains 20 percent to 80 percent by weight of water.

3. The bioreactor of claim 1 wherein said hydrogel polymer contains 50 percent to 60 percent by weight of water.

4. The bioreactor of claim 1 wherein said hydrogel polymer includes a cross linking agent in an amount of less than 5 percent.

5. The bioreactor of claim 1 wherein said bioreactant is a chelating agent.

6. The bioreactor of claim 5 wherein said chelating agent is deferoxamine mesylate.

7. The bioreactor of claim 1 wherein said hydrogel polymer is a poly(alkyl)methacrylate.

8. The bioreactor of claim 1 wherein said hydrogel polymer is formed as a flat sheet wound into a spiral scroll.

9. The bioreactor of claim 1 wherein said hydrogel polymer is formed as small pellets.

10. The bioreactor of claim 9 wherein said hydrogel polymer pellets are confined within the chamber in a mesh sack having mesh-size interstices smaller than the pellets.

11. The bioreactor of claim 1 wherein said hydrogel polymer is coated onto a solid adsorbent substrate.

12. The bioreactor of claim 11 wherein said solid adsorbent is activated carbon.

13. The bioreactor of claim 11 wherein said hydrogel polymer is formed by adding a competitively adsorbed solvent into a monomer-bioreactant mixture followed by polymerization of said monomer and replication to retain the bioreactant, with said competitively adsorbed solvent being subsequently removed to permit adsorption of the molecules of interest.

14. The bioreactor of claim 11 wherein said hydrogel polymer is coated onto a foam substrate.

15. The bioreactor of claim 14 wherein said gel-coated foam is employed along with a second adsorbent material.

16. The bioreactor of claim 14 wherein said chamber contains a plurality of gel-coated foams.

17. The bioreactor of claim 16 wherein each of said plurality of gel-coated foams contains a different bioreactant.

18. The bioreactor of claim 1 wherein there is added to the chamber a solvent capable of extracting said bioreactant.

19. The bioreactor of claim 18 wherein said bioreactant is deferoxamine mesylate and said solvent is ethyl alcohol irradiated with ultrasound.

20. The bioreactor of claim 1 wherein said hydrogel polymer is formed by polymerizing a monomeric material in the presence of said bioreactant and surrogate material.

21. The bioreactor of claim 20 wherein the ratio of bioreactant to surrogate is approximately 1:1.

22. A method of treating fluid by passing said fluid through a bioreactor of claim 1, whereby said fluid is reacted with said bioreactant.

23. A method for providing a bioreactor comprising:
   providing a chamber having contained therein a hydrogel polymer and a bioreactant, said bioreactant having been quenched by a displaceable surrogate material so that said hydrogel polymer forms around the bioreactant with sufficient intimacy to replicate its shape but without chemically attaching to or embedding said bioreactant, and
   supplying the chamber with means for contacting said bioreactant with fluid to be treated.

24. The method of claim 23 said hydrogel polymer contains 20 percent to 80 percent by weight of water.

25. The method of claim 23 said hydrogel polymer contains 50 percent to 60 percent by weight of water.

26. The method of claim 23 said hydrogel polymer includes a cross linking agent in an amount of less than 5 percent.

27. The method of claim 23 wherein said bioreactant is a chelating agent.

28. The method of claim 27 wherein said chelating agent is deferoxamine mesylate.

29. The method of claim 23 wherein said hydrogel polymer is a poly(alkyl)methacrylate.

30. The method of claim 23 wherein said hydrogel polymer is formed as a flat sheet wound into a spiral scroll.

31. The method of claim 23 wherein said hydrogel polymer is formed as small pellets.

32. The method of claim 31 wherein said hydrogel polymer pellets are confined within the chamber in a mesh sack having mesh-size interstices smaller than the pellets.

33. The method of claim 23 wherein said hydrogel polymer is coated onto a solid adsorbent substrate.

34. The method of claim 33 wherein said solid adsorbent is activated carbon.

35. The method of claim 23 wherein said hydrogel polymer is formed by adding a competitively adsorbed solvent into a monomer-bioreactant mixture followed by polymerization of said monomer and replication to retain the bioreactant, with said competitively adsorbed solvent being subsequently removed to permit adsorption of molecules of interest.

36. The method of claim 23 wherein said hydrogel polymer is coated onto a foam substrate.

37. The method of claim 23 wherein said hydrogel polymer is employed along with a second adsorbent material.

38. The method of claim 36 wherein said chamber contains a plurality of gel-coated foams.

39. The method of claim 38 wherein each of said plurality of gel-coated foams contains a different bioreactant.

40. The method of claim 33 further including the step of removing said bioreactant by immersing the hydrogel into a solvent capable of extracting said bioreactant, followed by drying said hydrogel.

41. The method of claim 40 wherein said bioreactant is deferoxamine mesylate and said solvent is ethyl alcohol irradiated with ultrasound.

42. The method of claim 23 wherein said hydrogel polymer is formed by polymerizing a monomeric material in the presence of said bioreactant and surrogate material.

43. The method of claim 42 wherein the ratio of bioreactant to surrogate is approximately 1:1.

44. A method according to claim 23 further comprising filling the chamber with substrate holding bioreactant sufficiently to immobilize the substrate and substantially avoid a pressure drop through the chamber.

45. A method according to claim 44 wherein the filling step comprises loading the chamber with a series of substrates, at least two of said substrates containing different bioreactants for reacting with body fluid, whereby different biochemical reactions take place within the same chamber.

46. A method according to claim 45 wherein the different biochemical reactions take place sequentially.

47. A method according to claim 23 comprising forming the hydrogel polymer with pores of greater size than the size of the bioreactant molecules.

48. A method according to claim 22 further comprising substantially filling available space in the chamber with foam.

49. A bioreactor capable of retaining therapeutic reactants and reaction products while confining reaction within the bioreactor comprising:
a chamber; a hydrogel polymer within said chamber; and a biomolecule within said chamber, said biomolecule having contacted a displaceable quenching surrogate material so that said hydrogel polymer forms around the biomolecule with sufficient intimacy to replicate its shape but without chemically attaching to or embedding said biomolecule.

50. The bioreactor of claim 49 wherein said biomolecule is heparin.

51. A method of treating fluid by passing said fluid through a bioreactor of claim 49, whereby said fluid is reacted with said biomolecule.

52. A method for providing a bioreactor which comprises passing blood through a chamber having a blood line connector at either end, said chamber having contained therein a hydrogel polymer and a biomolecule, said biomolecule having contacted a displaceable quenching surrogate material so that said hydrogel polymer forms around the biomolecule with sufficient intimacy to replicate its shape but without chemically attaching to or embedding said biomolecule.

53. The method of claim 52 wherein said biomolecule is heparin.

54. A method for treating a fluid comprising:
providing a chamber;
supplying said fluid to said chamber, wherein said chamber contains hydrogel polymer and a bioreactant which has been quenched by a displaceable surrogate material so that the hydrogel polymer forms around the bioreactant and holds it with sufficient intimacy to replicate its shape without chemically attaching to or embedding said bioreactant; and
reacting said fluid with said bioreactant.

55. A method according to claim 54 wherein the bioreactant is a chelating agent.

56. A method according to claim 55 wherein the fluid is blood and the chelating agent removes metal from the blood.

57. A method according to claim 54 wherein the hydrogel polymer holding the bioreactant is cast before placing it in the chamber.

58. A method according to claim 54 wherein the hydrogel polymer holding the bioreactant is sorbed onto a substrate.

59. A method according to claim 54 wherein the hydrogel polymer holding the bioreactant is sorbed onto an activated carbon substrate.

60. A method according to claim 54 wherein the hydrogel polymer holding the bioreactant is sorbed onto a foam substrate.

61. A method according to claim 54 wherein the hydrogel polymer comprises phantom shapes of bioreactant molecules, said shapes corresponding to shapes of bioreactant molecules previously held therein, said method comprising passing fluid containing bioreactant through the chamber containing said hydrogel polymer including said phantom shapes and removing bioreactant from the fluid by sorbing said bioreactant into said phantom shapes formed in the hydrogel polymer.

62. A method according to claim 54 wherein the bioreactant comprises a chelating agent.

63. A method according to claim 62 wherein the chelating agent comprises deferoxamine mesylate.

64. A method according to claim 54 wherein the hydrogel polymer comprises polyalkylmethacrylate.

65. A method according to claim 64 wherein the hydrogel polymer comprises polyhydroxyethylmethacrylate.

66. A method according to claim 54 comprising forming the hydrogel polymer around the bioreactant without causing any substantial steric hindrance.

67. A method according to claim 57 wherein the fluid is blood, the bioreactant held by the hydrogel polymer is deferoxamine mesylate, and the reacting step comprises removing metal from the blood by chelation with the deferoxamine mesylate.

* * * * *